United States Patent
Gramza et al.

(10) Patent No.: US 7,862,527 B2
(45) Date of Patent: Jan. 4, 2011

(54) EDGE BINDING FOR ORTHOPEDIC SUPPORTS AND METHOD OF USING SAME

(75) Inventors: Beth Gramza, Cincinnati, OH (US); Scott D. McCormick, Cincinnati, OH (US); Edward L. Weaver, II, Milford, OH (US)

(73) Assignee: 3M Innovative Properties Company, St. Paul, MN (US)

( * ) Notice: Subject to any disclaimer, the term of this patent is extended or adjusted under 35 U.S.C. 154(b) by 490 days.

(21) Appl. No.: 11/609,095

(22) Filed: Dec. 11, 2006

(65) Prior Publication Data

US 2007/0167891 A1 Jul. 19, 2007

Related U.S. Application Data

(60) Provisional application No. 60/749,767, filed on Dec. 13, 2005.

(51) Int. Cl.
*A61F 5/00* (2006.01)

(52) U.S. Cl. ............................................. 602/23

(58) Field of Classification Search ............. 602/20–23, 602/26–27, 60–62; 128/882
See application file for complete search history.

(56) References Cited

U.S. PATENT DOCUMENTS

| | | | |
|---|---|---|---|
| 2,002,527 A | 5/1935 | Dorogi et al. | |
| 3,408,438 A | 10/1968 | Staunton | |
| 3,926,186 A * | 12/1975 | Nirschl ........................ | 602/62 |
| 4,047,250 A | 9/1977 | Norman | |
| 4,212,746 A | 7/1980 | Tholema et al. | |
| 4,491,556 A | 1/1985 | Fujii et al. | |
| 4,573,455 A | 3/1986 | Hoy | |
| 4,603,690 A | 8/1986 | Skeen | |
| 4,626,185 A | 12/1986 | Monnet | |
| 4,726,362 A | 2/1988 | Nelson | |
| 4,844,057 A | 7/1989 | Hoy | |
| 4,844,094 A | 7/1989 | Grim | |
| 4,938,207 A | 7/1990 | Vargo | |
| 5,025,782 A | 6/1991 | Salerno | |
| 5,085,917 A | 2/1992 | Hodnett, III | |
| 5,139,477 A | 8/1992 | Peters | |
| 5,171,508 A | 12/1992 | Ishizu et al. | |
| 5,288,287 A | 2/1994 | Castillo et al. | |
| 5,326,523 A | 7/1994 | Gustavel et al. | |
| 5,385,538 A | 1/1995 | Mann | |
| 5,445,602 A | 8/1995 | Grim et al. | |

(Continued)

FOREIGN PATENT DOCUMENTS

FR 2 600 933 1/1988

*Primary Examiner*—Michael A. Brown
(74) *Attorney, Agent, or Firm*—Lisa P. Fulton

(57) ABSTRACT

An orthopedic support includes a sheet of flexible material having a proximal edge and a distal edge configured to extend at least partially around a portion of the wearer's anatomy and a pair of opposing lateral edges configured to at least partially enclose the portion of the wearer's anatomy. The orthopedic support includes at least one strap attached to the sheet of material and configured to extend over one of the lateral edges, wherein the strap comprises an associated fastening element configured to attach to the sheet of material so as to secure the sheet about the portion of the wearer's anatomy. The orthopedic support further includes an edge binding molded to an edge of the sheet of material.

26 Claims, 12 Drawing Sheets

U.S. PATENT DOCUMENTS

| | | | |
|---|---|---|---|
| 5,454,706 A | 10/1995 | Midorikawa et al. | |
| 5,462,517 A | 10/1995 | Mann | |
| 5,552,472 A | 9/1996 | Kerr et al. | |
| 5,626,557 A | 5/1997 | Mann | |
| 5,693,007 A | 12/1997 | Townsend | |
| 5,714,175 A | 2/1998 | Masui et al. | |
| 5,759,464 A | 6/1998 | Matsumoto et al. | |
| 5,823,981 A * | 10/1998 | Grim et al. | 602/26 |
| 5,997,793 A | 12/1999 | Lahnala | |
| 6,024,712 A | 2/2000 | Iglesias et al. | |
| 6,059,743 A | 5/2000 | Reinhardt et al. | |
| 6,214,261 B1 | 4/2001 | Smarto et al. | |
| 6,228,290 B1 | 5/2001 | Reames et al. | |
| 6,258,409 B1 | 7/2001 | Sale et al. | |
| 6,348,170 B1 | 2/2002 | Masui et al. | |
| 6,375,699 B1 | 4/2002 | Beck | |
| 6,398,903 B1 | 6/2002 | Stedron et al. | |
| 6,413,461 B1 | 7/2002 | Kobayashi et al. | |
| 6,471,276 B1 | 10/2002 | Brunsman et al. | |
| 6,479,006 B1 | 11/2002 | Kaufmann | |
| 6,482,167 B2 | 11/2002 | Grim et al. | |
| 6,558,590 B1 | 5/2003 | Stewart | |
| 6,630,043 B2 | 10/2003 | Sloot | |
| 6,743,188 B1 | 6/2004 | Littmann et al. | |
| 6,743,322 B2 | 6/2004 | Sloot | |
| 6,893,410 B1 | 5/2005 | Hely | |
| 7,237,270 B2 | 7/2007 | Crye et al. | |
| 2002/0163101 A1 | 11/2002 | Cotton et al. | |
| 2003/0176826 A1 | 9/2003 | Scott | |
| 2003/0204156 A1 | 10/2003 | Nelson et al. | |
| 2004/0031534 A1 * | 2/2004 | Schwartz | 139/169 |
| 2005/0020951 A1 * | 1/2005 | Gaylord et al. | 602/26 |

* cited by examiner

EDGE BINDING FOR ORTHOPEDIC SUPPORTS AND METHOD OF USING SAME

CROSS REFERENCE TO RELATED APPLICATIONS

The present application claims priority from U.S. Provisional Application No. 60/749,767 entitled EDGE BINDING FOR ORTHOPEDIC SUPPORTS AND METHOD OF USING SAME filed Dec. 13, 2005, the contents of which are incorporated herein by reference.

BACKGROUND OF THE INVENTION

1. Field of the Invention

Embodiments of the present invention are related to the field of orthopedic supports, and more particularly, to orthopedic supports having edge binding for increasing comfort and/or support for the wearer during use.

2. Description of Related Art

Current techniques for binding edges for orthopedic braces include, for example, stitching the edges of the brace material to form a seam. However, stitching may potentially loosen or snag, which may result in unraveling of the edges of the brace material. In addition, the stitching seams may be irritating to the skin when improperly secured to the brace material. Furthermore, stitching often requires additional fabrication steps and material that could be avoided, such as applying an extra piece of material along the peripheral edges of the brace material and then using thread to stitch the extra piece of material to the brace material.

Techniques have been developed to utilize flexible or polymeric material to bind the edges of a material to prevent fraying. For example, U.S. Pat. No. 6,482,167 to Grim et al. discloses a technique for forming orthopedic supports that includes impregnating the edges of casting material with a non-rigid bonding material, such as a flexible urethane or silicone rubber. The casting material is impregnated with water hardenable material such that the casting material forms a rigid and stiff construction. As a result, the bonding material aids in reducing irritation of the skin and prevents the casting material from fraying.

Moreover, stays or splints, which are used to provide support for the injured joint, are typically inserted within pockets or secured to the brace with additional fabric using stitching and the like. Techniques have been developed to reduce the amount of material and steps to construct an orthopedic support. For example, U.S. Pat. No. 6,024,712 to Iglesias et al. discloses orthopedic supports having a flexible sheet material and an exo-skeleton that is molded directly onto the flexible sheet material. The exo-structure is applied by injection molding to stiffen the support. As such, the exo-structure is typically a plastic that melts and permeates into the pores of the sheet material such that the plastic bonds to the sheet material after cooling.

Despite these improvements in reducing fabrication materials and steps, additional innovations in orthopedic supports to promote better comfort and/or support for the wearer are also desired. In particular, although techniques other than stitching have been utilized to bind the edges of material, edge binding that is conducive for orthopedic supports having soft and flexible laminate or non-laminate materials is desired. Moreover, despite methods for stiffening orthopedic supports, improvements in adding stays or splints to stiffen the orthopedic support and provide support for the wearer is desired.

It would therefore be advantageous to provide an orthopedic support that imparts increased comfort and/or support for the wearer. In addition, it would be advantageous to provide an orthopedic support that includes edge binding that is capable of exhibiting rigidity or pliability for various orthopedic applications.

BRIEF SUMMARY OF THE INVENTION

Embodiments of the present invention address the above needs and achieve other advantages by providing an orthopedic support for supporting a portion of a limb of the wearer. The orthopedic support generally includes a sheet of flexible material for conforming to a portion of the wearer's anatomy, as well as straps and associated fastening elements for securing the sheet of material on the wearer. The support includes edge binding that may be secured at various locations on the sheet of material to provide comfort and/or support, as well as rehabilitate the supported area. The edge binding is preferably a polymeric material capable of exhibiting rigidity or pliability.

In one embodiment, a knee support of the present invention includes a sheet of material including a plurality of straps for securing the sheet of material about a wearer's knee. The knee support includes at least one stay secured to an edge of an opening defined in the sheet of material to provide support and rehabilitation to the wearer's knee.

The sheet of material, according to one variation of the present invention, is generally rectangular and includes opposing lateral edges and opposing proximal and distal edges. The sheet of material is configured to wrap about a wearer's knee between the thigh and calf, and may include a patellar opening for accommodating a wearer's patella. The sheet of material could be a laminate or non-laminate material.

The knee support includes a plurality of straps that may be formed integral to the sheet of material. Typically, a pair of straps extends from a first lateral edge and proximate to each of the proximal and distal edges of the sheet of material, while a third strap extends from an opposite lateral edge approximately midway between the top and bottom edges. Each of the straps includes fastening elements on a free end that attaches to complementary fastening material on the sheet of material.

The knee support may also include a plurality of bladders interconnected with conduit that carries air supplied by a pump to each of the interconnected bladders. The inflatable bladder typically includes a pump operable to inflate the bladder to a desired pressure, as well as a release valve for selectively releasing pressure from the bladder. The bladder may include a patellar bladder that substantially encircles the patella, as well as medial and lateral bladders that extend on respective medial and lateral sides of the knee. Furthermore, each of the medial and lateral bladders may be configured to extend adjacent to at least one stay. In one variation, the knee support includes a bladder cover secured to an inner surface of the sheet of material that encloses the bladder and secures the bladder in a predetermined position.

The knee support includes at least one stay secured to an edge of an opening defined in the sheet of material. In one aspect, the knee support includes a plurality of stays. At least one stay typically extends on each of the medial and lateral sides of the wearer's knee. A pair of stays may be aligned approximately end-to-end in a proximal-distal direction, although a small gap is usually located between each pair of stays. Moreover, each stay may be configured to conform to the natural flexion of the knee between the thigh and calf.

Each stay may also include thinner material portions or openings defined therein. In addition, each stay is typically injection molded within a respective opening.

The knee support could include an edge material secured about the outer periphery of the sheet of material and/or a patellar opening. The edge material engages the edges of the sheet of material. The edge material is generally a soft polymeric material that does not reduce the pliability or flexibility of the sheet. The edge material may be injection or compression molded to the sheet of material.

Embodiments of the present invention may provide many advantages. For instance, the edge binding may be secured to the edges of the sheet of material for increasing comfort and/or support. Moreover, the edge binding eliminates additional material and fabrication steps to manufacture orthopedic supports, such as by eliminating stitching and pockets. The edge binding may be pliable and flexible or semi-rigid such that the edge binding is adaptable for various degrees of flexibility, support, and rehabilitation. Furthermore, the edge binding is adaptable for different orthopedic supports, such as a knee support.

The edge binding is capable of "grabbing" the edges of the sheet of material such that the edge binding may be secured to any number of locations on the sheet of material. In particular, the edge binding may be secured about the edges of the sheet of material to prevent fraying. The edge binding may be pliable such that the flexibility of sheet of material is not sacrificed. Another embodiment of the present invention provides edge binding configured as stays that may be formed at various locations on orthopedic supports for increasing support. The stays may be secured to the sheet of material within openings defined in the sheet of material by grabbing the edges of the openings. In addition, the positioning of the stays is capable of increasing the rehabilitative effects of various supports, such as by supporting the medial and lateral sides of the knee.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Generally, embodiments of the present invention provide an orthopedic support that includes a sheet of flexible material for wrapping about and conforming to a portion of a wearer's anatomy. One or more straps having a fastening element thereon are configured for securing the sheet of material about the wearer's anatomy. In addition, the orthopedic support includes edge binding, generally polymeric material, that may be secured to the sheet of material at various locations. The edge binding is capable of binding to the edges of the sheet of material to provide the wearer with increased comfort and/or support depending on the properties of the polymeric material selected.

Thus, the term "edge binding" is not meant to be limiting, as the edge binding could be configured as a rigid or semi-rigid member, such as stays or splints for increasing the rigidity and support of the orthopedic support. In addition, the edge binding could be a soft and flexible material, such as edge material that is secured to the outer edges and/or openings defined within the sheet of material to prevent fraying and irritation of the skin. Therefore, the edge binding is adaptable for use with various orthopedic supports. The orthopedic support could be worn on a limb or portions of a limb of a wearer, such as, for example, on a wrist, knee, elbow, back, arm, forearm, leg, or thigh.

Figure 1:
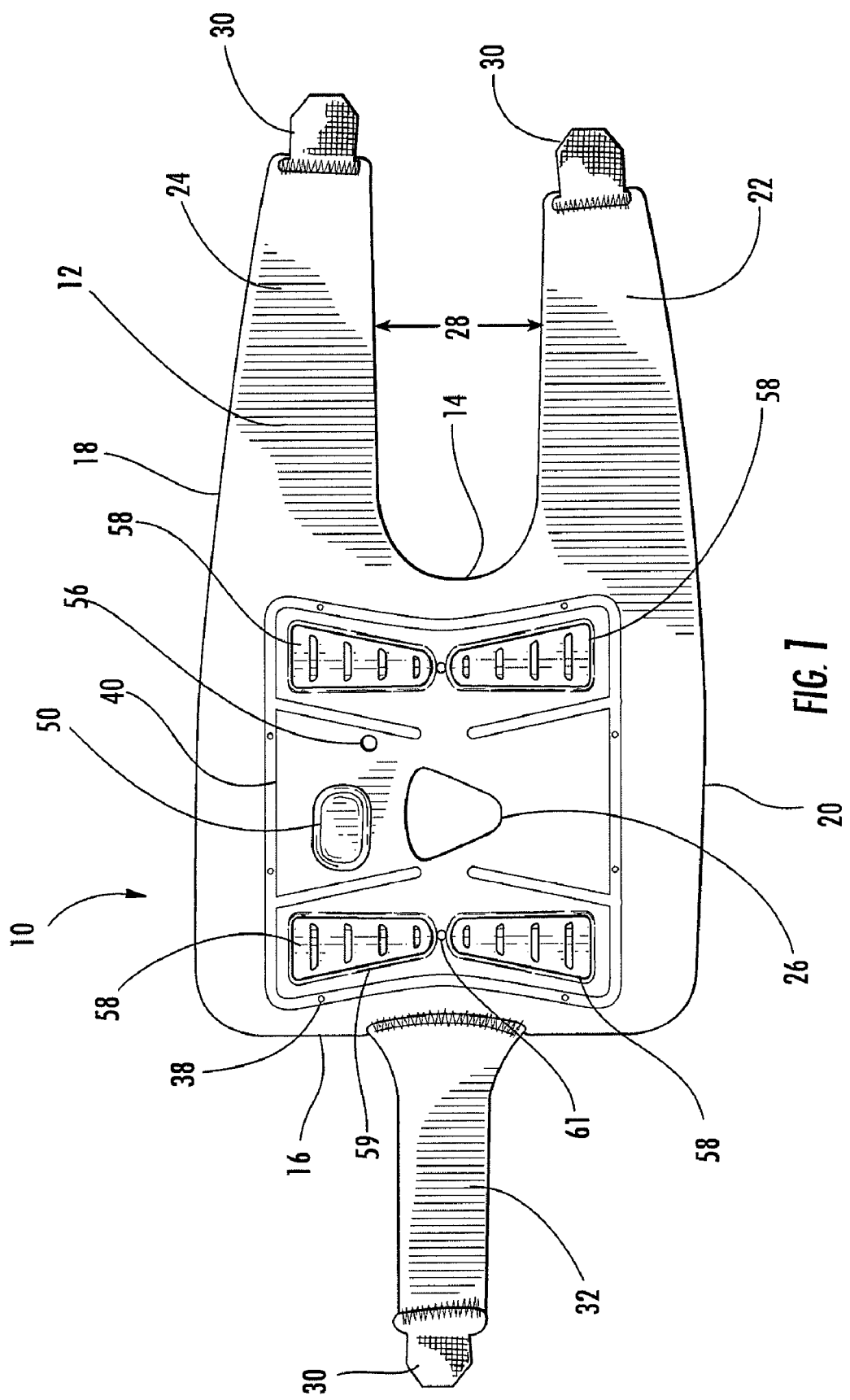
FIG. 1 is a plan view of an outer surface of a knee support, according to one embodiment of the present invention.

Referring now to the drawings and, in particular, to FIG. 1, there is shown a knee support 10. The knee support 10 is designed to wrap around a wearer's knee between the wearer's thigh and calf. The knee support 10 is adjustable with a plurality of straps that allow the knee support to be custom fitted depending on the size of the wearer's leg. In addition, the knee support 10 is easy to fit and remove, as the knee support is a generally planar structure that is wrapped around the wearer's leg instead of being pulled up the wearer's leg like a sleeve.

As shown in FIG. 1, the knee support 10 according to one embodiment includes a sheet of material 12 constructed of a laminate material having multiple plies, including a soft, skin-friendly inner layer, a foam middle layer, and an outer layer. Advantageously, the inner layer is worn against the skin and has a low skin irritant, soft feel, and can have moisture-wicking properties, while portions of the outer layer allows attachment of complementary fastening elements 30, as discussed below. For example, the sheet of material 12 could be a laminate of polyester hook engaging loop material, a polyurethane foam, and a polyester jersey knit material.

The sheet of material 12 includes opposing lateral edges 14, 16 and opposing top and bottom edges 18, 20, respectively. According to one embodiment, the area defined by the lateral ends and edges is approximately 10"×11", although the sizing may vary depending on the application and wearer of the knee support 10. However, it is preferred that the sheet of material 12, as defined above, remains generally rectangular or square in dimension. The lateral edge 16 is relatively flat or linear and intersects the top 18 and bottom 20 edges at approximate right angles. In one embodiment, the opposing top 18 and bottom 20 edges are substantially parallel to one another, although a slight taper occurs at a pair of integral straps 22, 24, as discussed below. The sheet of material 12 also defines a patellar opening 26 that is located generally in the center of the sheet of material. The patellar opening 26 is generally triangular with rounded corners, where the apex of the patellar opening extends distally when the opening is placed over a wearer's patella.

The knee support 10 includes a pair of laterally extending top and bottom straps 22, 24, respectively, that are integral with the sheet of material 12 and extend from the lateral edge 14 of the sheet of material. In one embodiment, each of the integral straps 22, 24 has a fastening element 30 attached thereto. The fastening element 30 preferably includes fastening material on one surface for mating with complementary fastening material on the sheet of material 12. As mentioned above, the integral straps 22, 24 have a slightly tapering outer edge. The inner edge of the integral straps 22, 24 is also tapering or curved such that the straps define a gap 28 therebetween at the lateral edge 14 of the sheet of material 12. The gap 28 according to one embodiment of the present invention is about 4½ inches at the widest point. Furthermore, integral strap 22 may be slightly shorter than integral strap 24. In this regard, integral strap 24 is typically placed above the knee and about the wearer's thigh, while the shorter integral strap 22 is positioned below the knee and about the wearer's calf. In one embodiment, integral strap 22 is about 7½ inches in length measured from lateral edge 14, while integral strap 24 is about 8 inches in length.

The knee support 10 also includes a lateral edge strap 32 that extends from the lateral edge 16 of the sheet of material 12 in a direction opposite the integral straps 22, 24. The lateral edge strap 32 is positioned approximately midway between the top 18 and bottom 20 edges such that the lateral edge strap is capable of wrapping behind a wearer's knee and overlapping the lateral edge 14 in the gap 28 defined by the upper and lower integral straps. Unlike the integral straps 22, 24, the lateral edge strap 32 is attached to the sheet of material 12 with stitching. The lateral edge strap 32 of the knee support 10 includes a fastening element 30 attached to its free end. In one embodiment, the lateral edge strap 32 is approximately 6½ inches in length measured from the lateral edge 16.

The aforementioned features of the knee support 10 are not meant to be limiting, as there may be many modifications in alternative embodiments of the present invention. For instance, there may be any number of integral 22, 24 and lateral edge 32 straps in various embodiments of the present invention to provide a range of support for the wearer. Thus, there could be one or more integral straps 22, 24 defined along the lateral edge 14, and one or more lateral edge straps 32 defined along the lateral edge 16. Furthermore, each of the integral 22, 24 and lateral edge 32 straps may be various sizes and configurations for accommodating different sizes of wearers. For example, although the lateral edge strap 32 is shown as being formed of a separate material and affixed to the sheet of material 12, the lateral edge strap could be formed integral with the sheet of material.

An outer surface of the sheet of material 12 includes a fastening material that is complementary to fastening material carried by the fastening elements 30. Typically, the fastening material of the fastening elements, as well as the fastening material on the outer surface of the sheet of material 12, are constructed of a complementary hook and loop material such as VELCRO®. However, the term "fastening material," as used herein, denotes any type of chemical, mechanical, or other fastener that allows connection of two separate components, such as snaps, hook and loop connectors, adhesives, buckles, etc. Notably, the fastening material of the fastening elements 30 (hooks), and the fastening material (loops) of the outer surface of the sheet of material 12 mate to, and attach with, one another when brought into contact. These fastening materials, therefore, are referred to herein as being complementary.

The opposite surface of the fastening material of the fastening elements 30 is a flexible polymeric support. The fastening material is attached to the polymeric support with an adhesive or similar attachment technique. Therefore, the polymeric support provides increased support and durability for the fastening elements 30, which are typically unsupported. The polymeric support could be a polymeric material, such as polyethylene, and formed by injection molding or compression molding. In one aspect of the present invention, the fastening elements 30 are secured to a respective strap by injection molding the polymeric support directly to the integral 22, 24 and lateral edge 32 straps. However, the fastening elements 30 could be attached with similar techniques or combination of techniques, such as with an adhesive, stitching, RF welding, etc. It is understood that the fastening material of the fastening elements 30 are not required to be supported by polymeric supports, which is typical of most conventional fastening elements. For a further discussion of the fastening elements, see U.S. patent application Ser. No. 11/609,115, entitled "Fastener Tabs and Strapping System for Orthopedic Supports and Method of Using Same," which is assigned to the present assignee and incorporated herein by reference.

Figure 2:
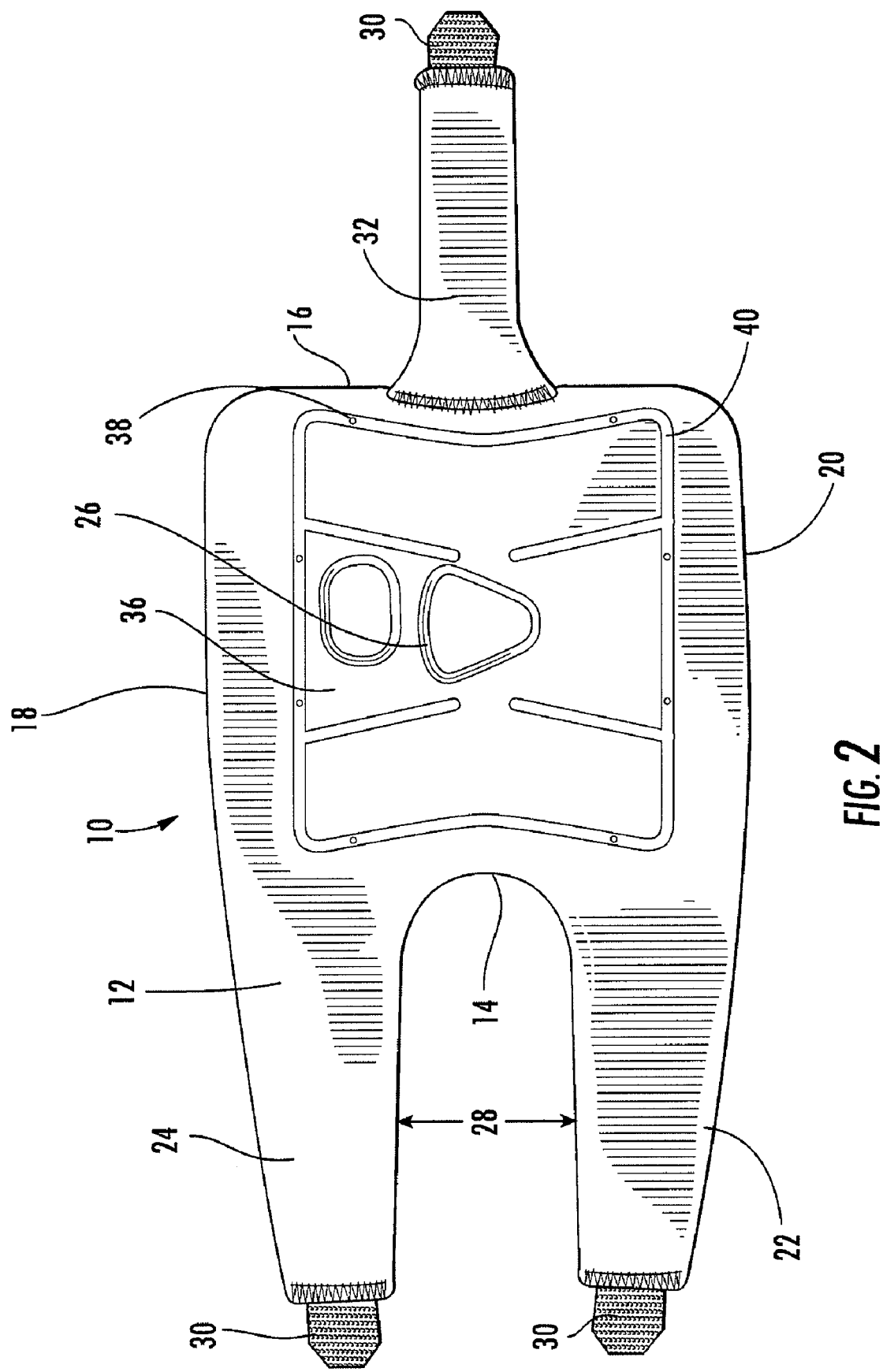
FIG. 2 is a plan view of an inner surface of the knee support shown in FIG. 1.
Figure 3:
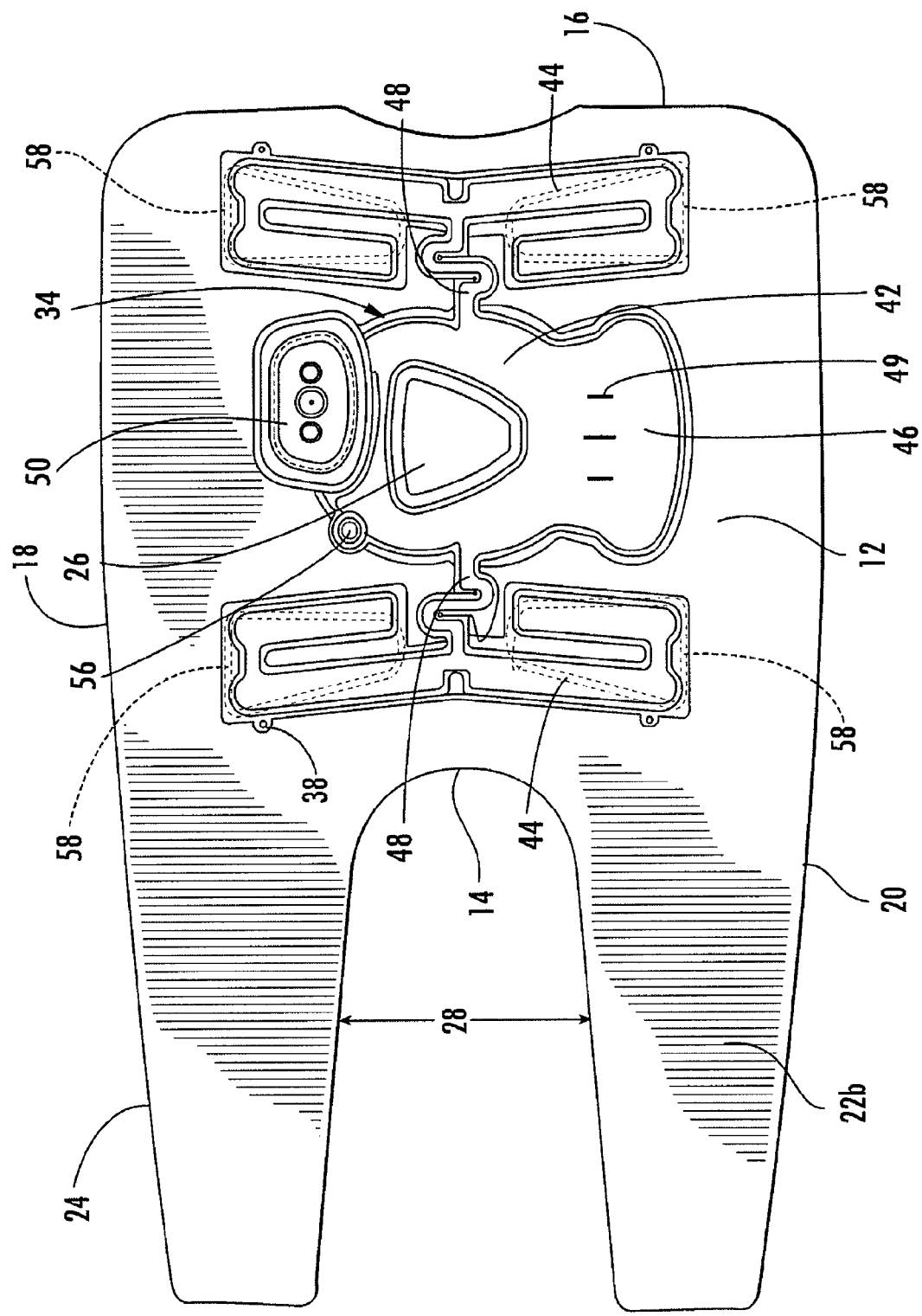
FIG. 3 is a plan view of a knee support having an inflatable bladder positioned on an inner surface of a sheet of material, according to one embodiment of the present invention.

The knee support 10 also includes an inflatable bladder 34, as shown in FIG. 3. The inflatable bladder 34 is positioned on an inner surface of the sheet of material 12 and is encased, or otherwise enclosed, by a bladder cover 36, as depicted in FIG. 2. As such, the bladder cover 36 prevents the inflatable bladder from moving out of a predetermined position on the sheet of material 12. The bladder cover 36 may be any suitable skin-friendly material, such as polyester, nylon, or a polyester/spandex blend. FIG. 2 demonstrates that the bladder cover 36 is configured in a substantially rectangular shape and includes an opening that conforms to the patellar opening 26. However, the bladder cover 36 could be various sizes and configurations in aspects of the present invention. For example, the bladder cover 36 could substantially cover the entire sheet of material 12 or only portions of the inflatable bladder.

The bladder cover 36 is typically attached to the sheet of material 12 with RF welding, although the bladder cover could be attached to the sheet of material with any suitable technique or combinations of techniques, such as stitching, spray adhesive, adhesive film, etc. For example, the bladder cover 36 could be pre-coated with a polyurethane adhesive over its entire inner surface. Moreover, the bladder cover 36 could be attached to the sheet of material 12 using at least a portion of the inflatable bladder 34 as an adhesive, such as by RF welding proximate to pin holes 38 defined in the inflatable bladder. The remaining portions of the bladder cover 36 could then be secured to the sheet of material 12 using an adhesive. In addition, the inflatable bladder 34 could be directly attached to the inner surface of the sheet of material 12, or at least partially attached to the sheet of material, such as with RF welding or adhesive. FIGS. 1-3 illustrate that pin holes 38 are employed to locate the inflatable bladder 34 within the mold and on the sheet of material 12 prior to securing the bladder cover 36 to the sheet of material 12. An indentation 40 is formed in both the bladder cover 36 and the sheet of material 12 about the periphery of the bladder cover indicating where the bladder cover is secured to the sheet of material.

The inflatable bladder 34 substantially surrounds the patellar opening 26, and may include various configurations of interconnected bladders in fluid communication with one another. FIG. 3 depicts an inflatable bladder 34 having a patellar bladder 42 and a pair of stay bladders 44. In this regard, each of the patellar 42 and stay 44 bladders are in fluid communication with one another. The patellar bladder 42 generally surrounds the patellar opening 26 and includes a bottom portion 46 that extends downwardly from the patellar opening. The bottom portion 46 includes spot welds 49 that are utilized to define channels and raised portions. Each of the stay bladders 44 includes channels generally arranged in a C-shape. When the knee brace 10 is worn, the stay bladders 44 align with the medial and lateral portions of the knee, as well as stays 58, which are discussed in further detail below.

Figure 4:
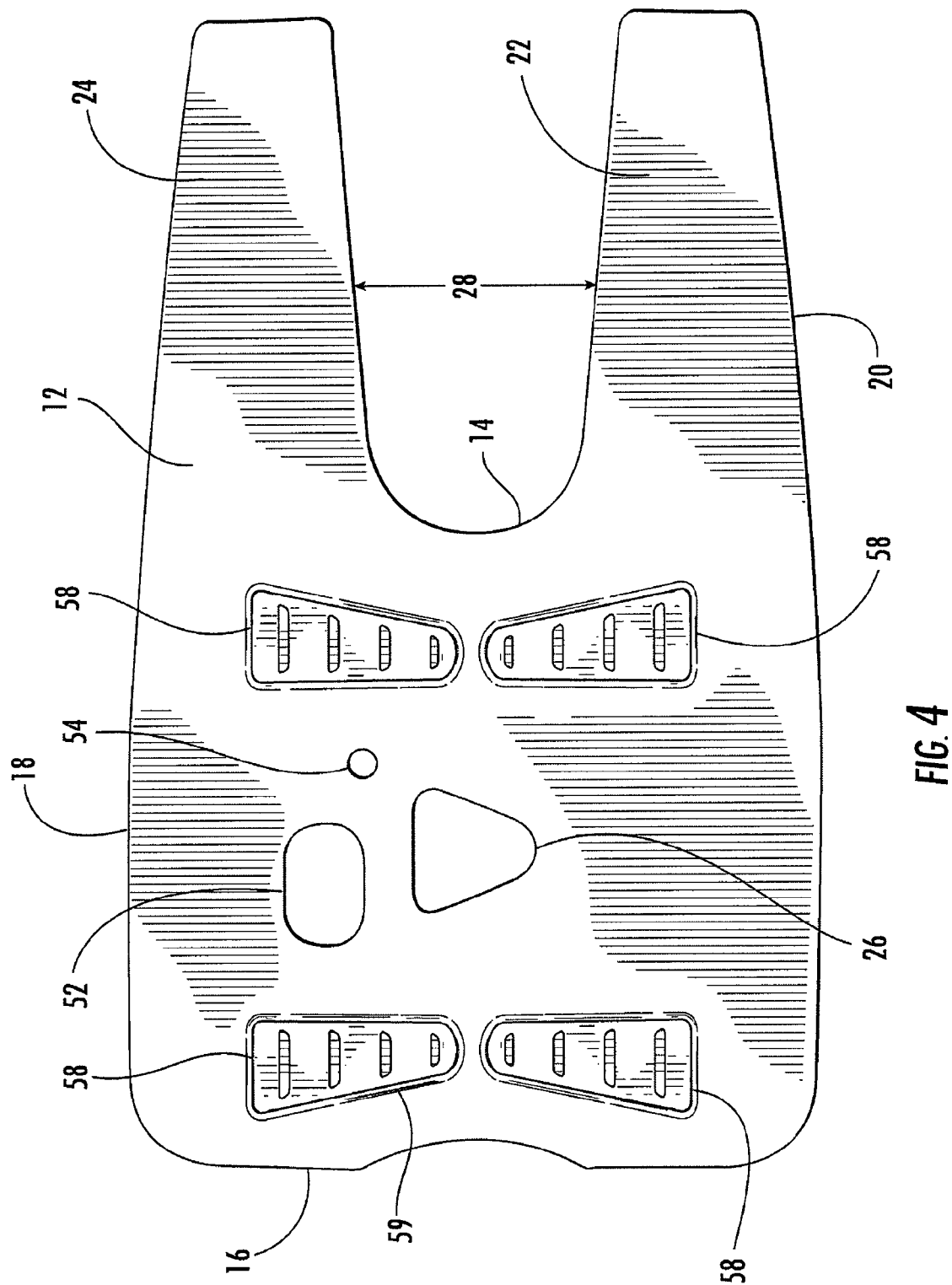
FIG. 4 is a plan view of an outer surface of a blank of sheet of material having stays secured thereto, according to one embodiment of the present invention.
Figure 5:
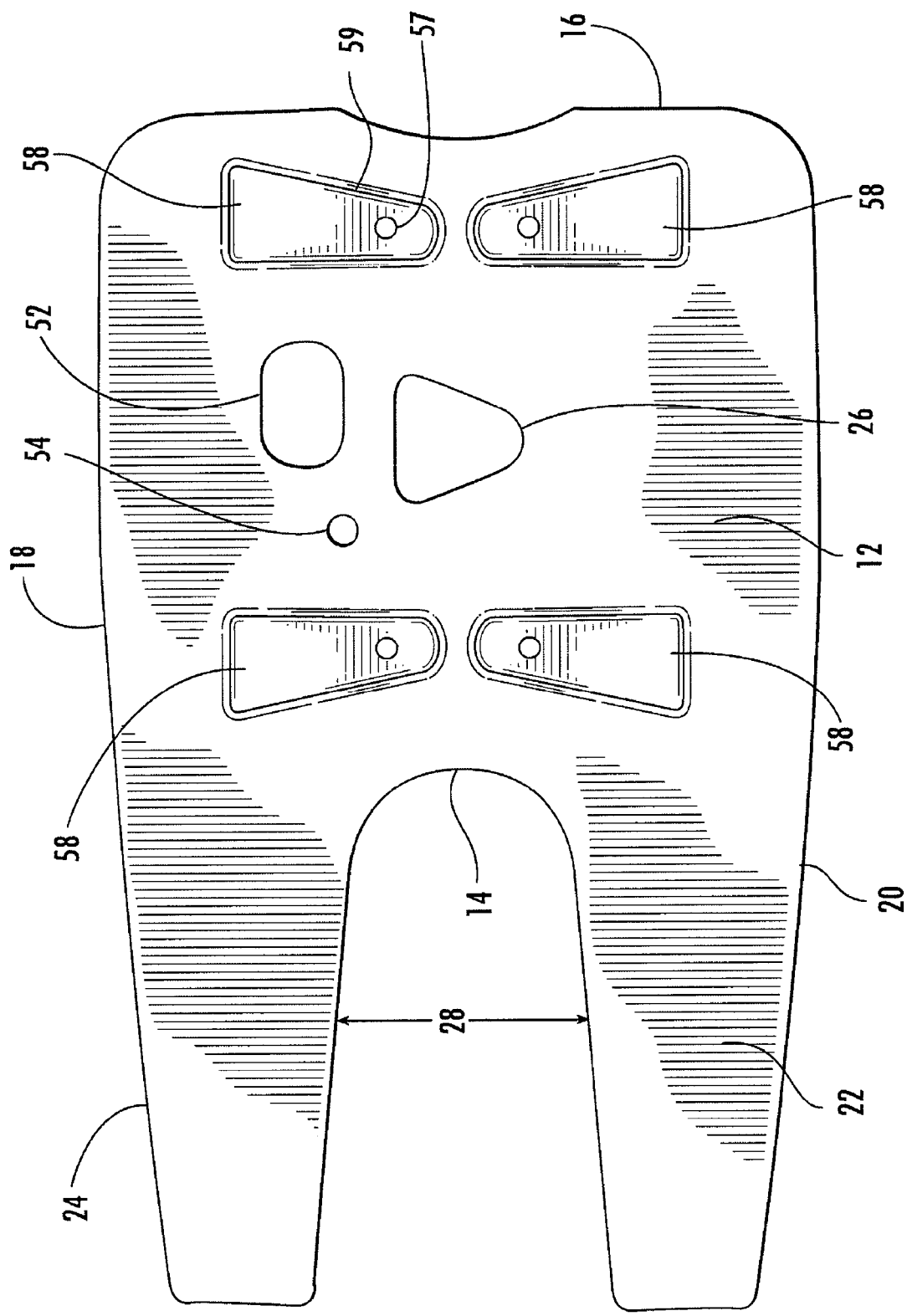
FIG. 5 is a plan view of an inner surface of the blank of sheet of material shown in FIG. 4.

FIG. 3 illustrates that a pump 50 is in fluid communication with the inflatable bladder 34. A conduit 48 carries air supplied by the pump 50 to each of the stay bladders 44. An opening 52 is defined in the sheet of material 12 for readily locating and accessing the pump 50, as shown in FIGS. 4 and 5. Moreover, the sheet of material 12 also includes a small hole 54 that corresponds to the size of a release valve 56, such that the release valve protrudes through the hole to remain accessible by the wearer. A washer (not shown) is typically positioned around the circumference of the release valve 56 to provide support and proper positioning of the release valve. The washer could be injected molded directly to the sheet of material 12 or be configured to fit over the release valve. Furthermore, a back plate (not shown) is typically employed to support the pump 50. The back plate is secured to the pump 50, such as with an adhesive, to provide support during operation of the pump.

The inflatable bladder 34 is formed by RF welding layers of air impermeable material to form the shape shown in FIG. 3. The pump 50 includes a flexible thermoplastic material having an air inlet hole defined in a surface of the pump. The pump 50 could have an open-cell foam material encased therein to aid in pumping and replenishing the pump chamber. The pump 50 operates by covering the air inlet and squeezing the pump such that air is forced into the inflatable bladder 34. Air is forced through a check valve, and pressure within the inflatable bladder 34 causes the check valve to close to prevent air from escaping the bladder through the check valve. The pump 50 is replenished by uncovering the air inlet hole. Typically, the inflatable bladder 34 is filled by repeatedly squeezing the pump 50 until a desired amount of pressure is achieved. Air is released from the bladders by depressing the release valve 56.

It is understood that the inflatable bladder 34 should not be limited to any particular size or configuration shown in FIG. 3. For instance, the inflatable bladder 34 could be pre-inflated such that a pump 50 and release valve 56 are optional. In addition, the inflatable bladder 34 could include one of a patellar bladder 42, stay bladders 44, or various other bladders positioned on the sheet of material 12. Furthermore, although an inflatable bladder 34 is preferred, it is understood that various techniques could be used for increasing comfort, such as with foams, gels, pads, or any other suitable cushioning or padding material.

The knee support 10 also includes a plurality of stays 58 secured to the sheet of material 12. The stays 58 are generally positioned on opposite sides of the patellar opening 26. When the knee support 10 is secured to the wearer's knee, the stays 58 are rendered relatively immobile on the medial and lateral sides of the knee and provide reinforcement for the knee. Furthermore, if an inflatable bladder 34 is employed, the stays 58 are positioned adjacent to the stay bladders 44, as shown in FIG. 3. Thus, the stay bladders 44 provide increased cushioning and comfort adjacent to the stays 58.

FIG. 1 demonstrates that a pair of stays 58 is positioned on each side of the patellar opening 26. Each pair of stays 58 is aligned generally end-to-end, although a small gap is present between each stay. A small circular member 61 could be positioned within the gap between each pair of stays 58. Each pair of stays 58 is positioned in a proximal-distal direction such that each pair collectively extends along the medial and lateral sides of the knee. As shown, each of the stays 58 is generally trapezoidal and has an angled edge 59, such as 5°-15°, that is biased toward the patellar opening 26 such that when the knee support 10 is worn, the stays conform to a more natural position compared to stays that are flat and longitudinal. For example, each of the stays 58 may be approximately 3 inches in length, 1 inch in width at its wider end, and ½ of an inch at its narrower end. There could be a gap of about ¼ to ½ of an inch between each pair of stays 58.

Figure 7:
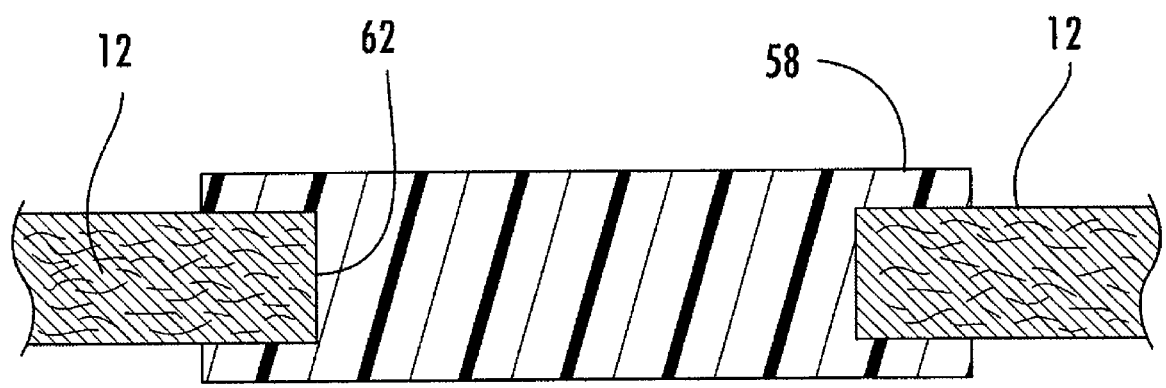
FIG. 7 is a cross-sectional view of a stay secured to the knee support shown in FIG. 1.

FIGS. 4 and 5 illustrate the sheet of material 12 without the inflatable bladder 34 or bladder cover 36 secured thereto. Thus, when secured to the sheet of material 12, each of the stays 58 extends completely through the sheet of material. As shown in FIG. 7, each of the stays 58 "grabs" the edge of the opening defined through the sheet of material 12. In this regard, each of the stays 58 includes a substantially C-shaped cross section about its perimeter. As a result, each stay 58 encapsulates an edge 62 of the sheet of material 12 about the entire periphery of the opening in the sheet.

Figure 6:
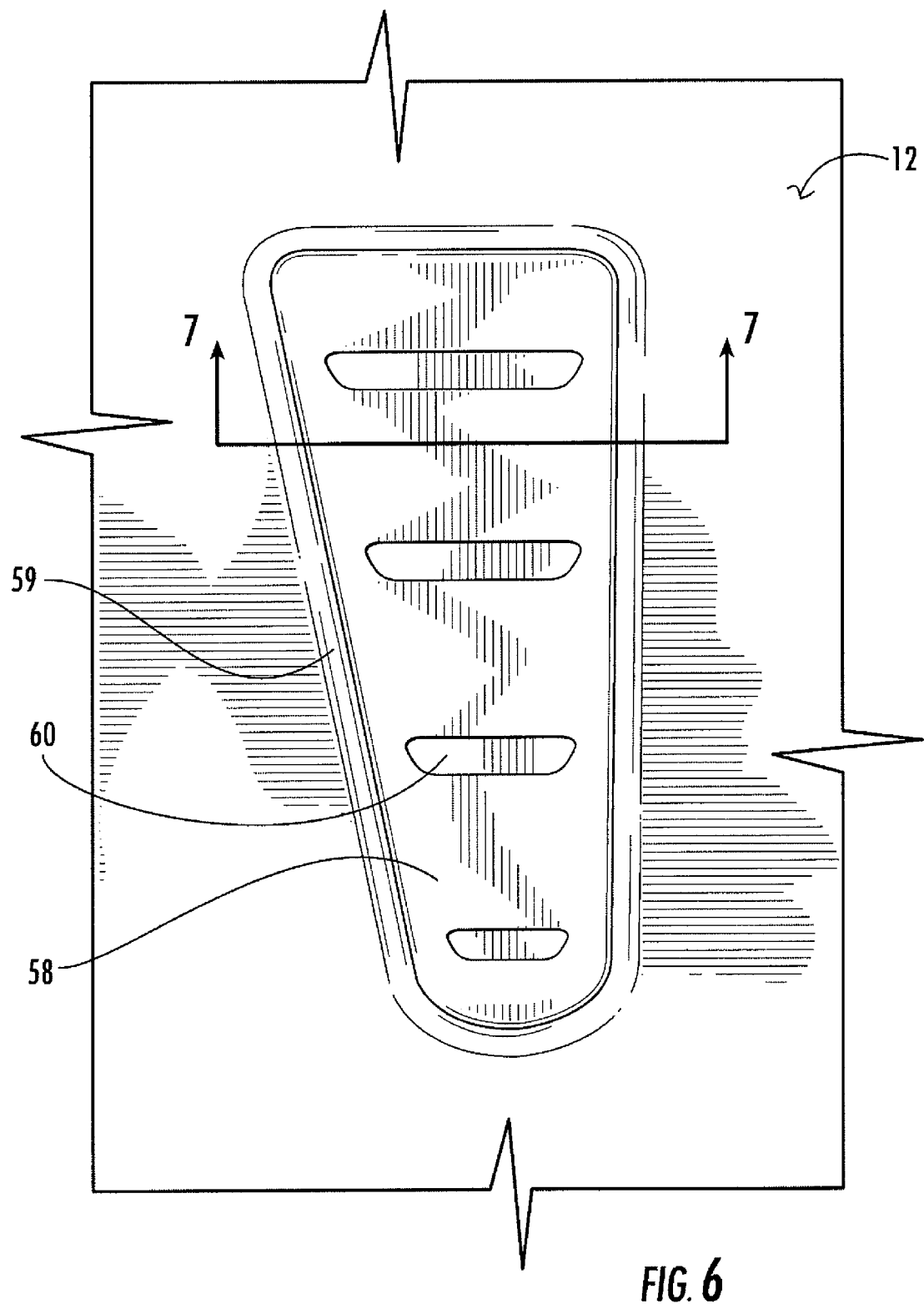
FIG. 6 is an enlarged view of a stay secured to the sheet of material of the knee support shown in FIG. 1.

FIG. 6 shows that each stay 58 includes a reduced material portion 60 that is of a reduced thickness compared to the remaining portions of the stay. The reduced material portions 60 are generally trapezoidal in configuration. The reduced thickness facilitates greater flexibility, lighter weight, and reduced material consumption. As shown in FIG. 5, the opposite surface of the stays 58 is generally smooth. Thus, the smooth portion of the stays 58 lies adjacent to the stay bladders 44 when the inflatable bladder 34 is secured to the sheet of material 12.

The stays 58 are typically formed of a polymeric material, such as low density polyethylene ("LDPE"). The stays 58 are semi-flexible such that the stays provide support while also allowing some range of motion during use. The stays 58 are formed and secured to the sheet of material 12 with injection molding, compression molding, or similar technique. The inflatable bladder 34 is positioned on the sheet of material 12 such that the pin holes 38 of the inflatable bladder align with the pin holes of the sheet of material and bladder cover 36. The pump 50 and release valve 56 are also aligned with respective holes 52 and 54 defined in the sheet of material 12. The inflatable bladder 34 and bladder cover 36 are then secured to the sheet of material 12 with any suitable technique, as described above.

Figure 9:
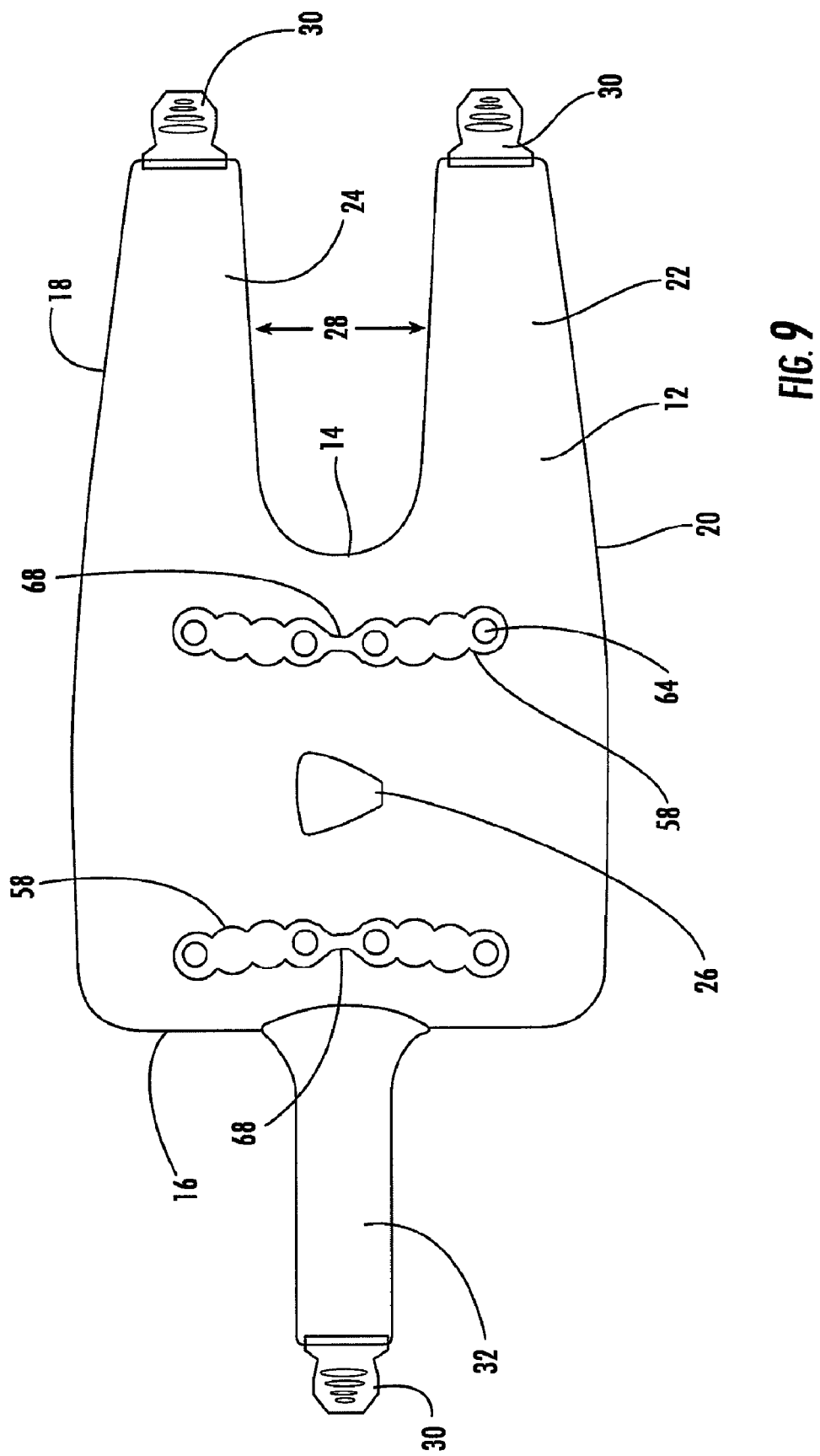
FIG. 9 is a plan view of a knee support according to another embodiment of the present invention, illustrating stays secured to a sheet of material.
Figure 10:
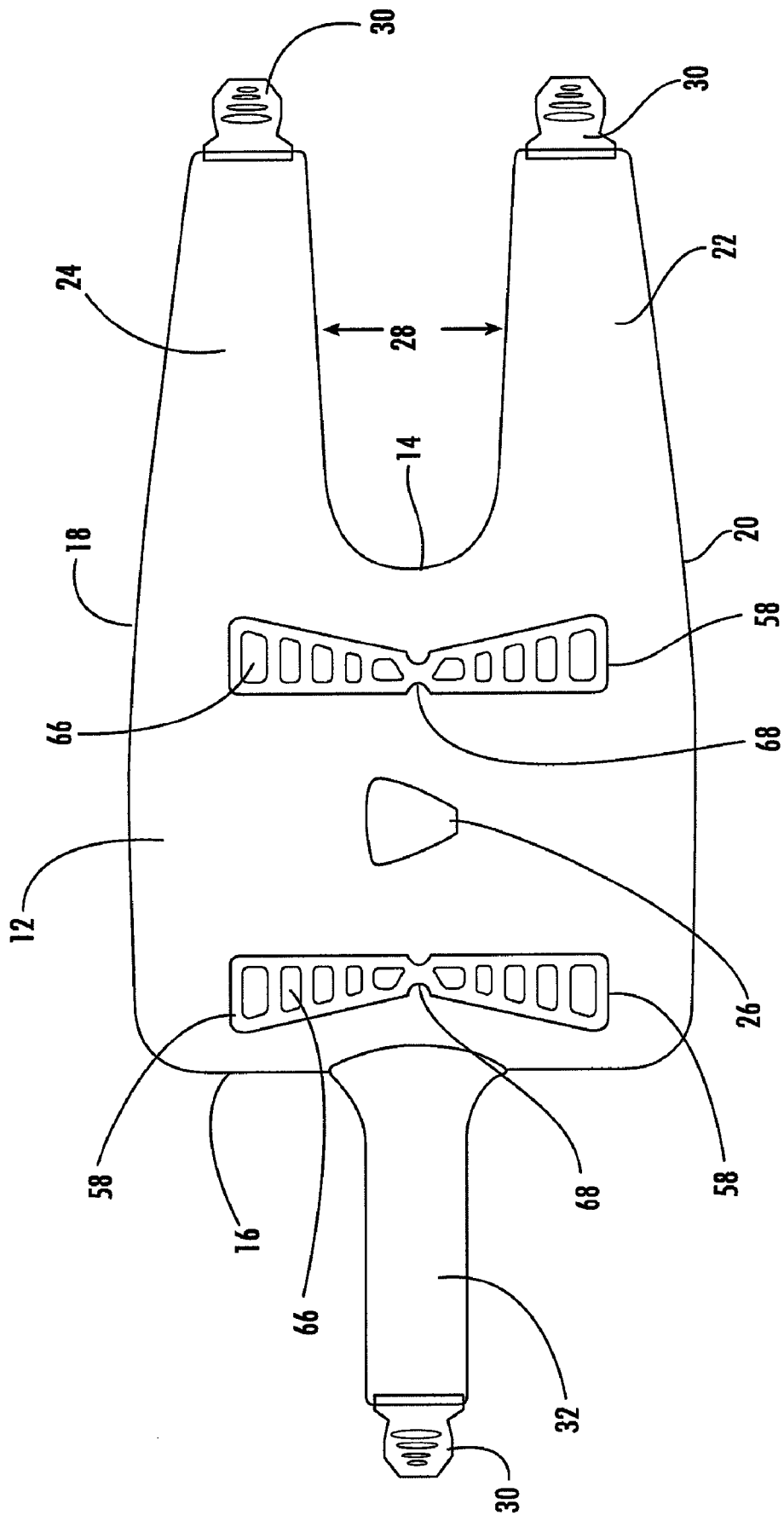
FIG. 10 is a plan view of a knee support according to another embodiment of the present invention, illustrating stays secured to a sheet of material.

The stays 58 may be various sizes and configurations in additional aspects of the present invention. For example, FIG. 9 illustrates that a single stay 58 could be positioned on each side of the patellar opening 26. Each stay 58 includes a tapered portion 68 extending between proximal and distal portions of the stay. Thus, each stay 58 is longitudinal and unitary, while also including a tapered portion 68 for promoting flexion and flexibility proximate to the knee joint. Each stay 58 includes a curvature that substantially aligns with the natural flexion of the knee between the thigh and calf. In addition, FIG. 9 illustrates that each stay 58 includes holes 64, which provides similar benefits to the reduced material portions 60 described above. Similarly, FIG. 10 depicts another aspect where each stay 58 is similar to a pair of stays described with respect to FIGS. 1-8. However, the stays 58 shown in FIG. 10 include a tapered portion 68 extending between proximal and distal portions such that each stay 58 is a unitary member. The stays 58 are also slightly tapered to accommodate the natural flexion of the knee, as discussed previously. The stays 58 also include slots 66 to increase flexibility of the knee support 10, while also reducing weight and the amount of material required.

Moreover, although the stays 58 are shown as being generally trapezoidal and including a biased or angled edge that conforms to the natural flexion of the knee, it may also be possible for the stays to be straight if desired. The stays 58 may also be a solid member such that reduced material portions 60, holes 64, and/or slots 66 are not required. Furthermore, there may be any number of stays 58 in alternative embodiments of the present invention, and the stays may be positioned at any desired location on the sheet of material 12. Thus, the stays 58 are capable of engaging and encapsulating an edge of the sheet of material 12 within various openings defined in the sheet of material to achieve a desired amount of support. Furthermore, although the stays 58 are described as being semi-flexible, it is understood that the stays could be rigid in additional aspects of the present invention, such as where further support is required. The circular member 61 could be various configurations and extend between a pair of stays 58, and may be secured to the outside of the sheet of material 12 or completely through the sheet of material (i.e., similar to the stays) using injection molding. However, the circular member 61 could also be omitted such that the circular member is optional.

Figure 8:
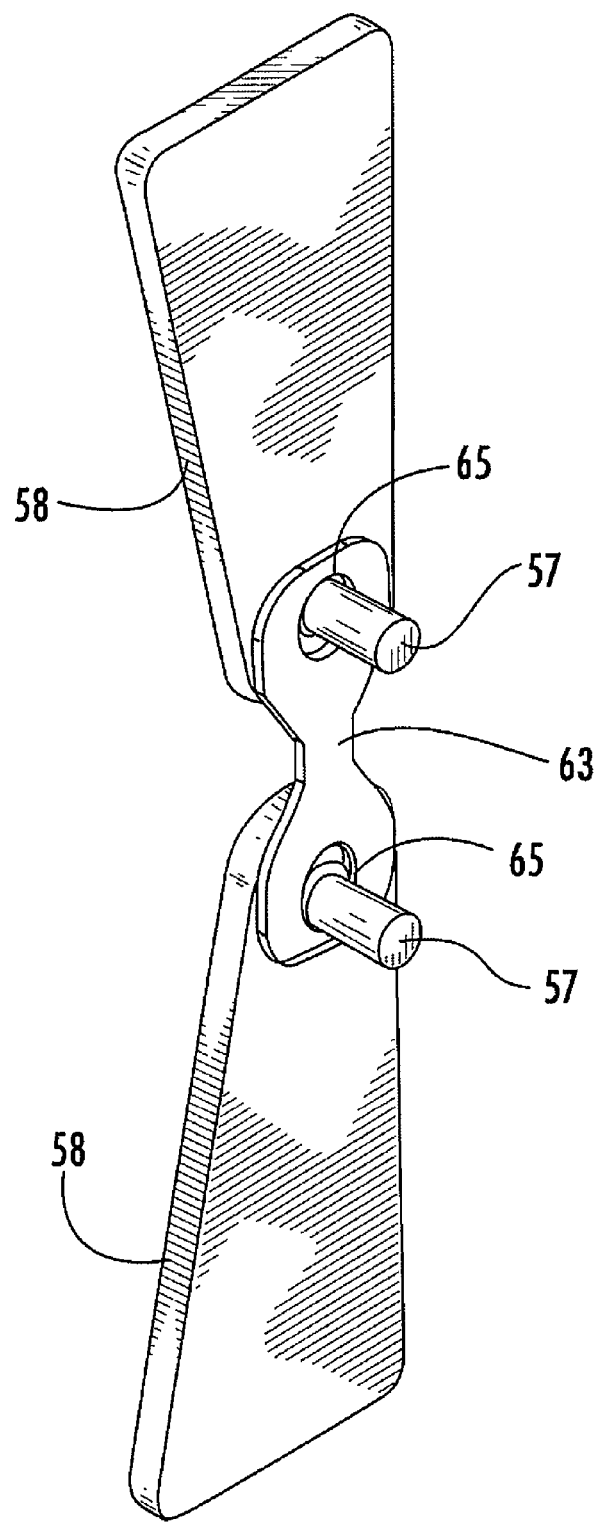
FIG. 8 is a perspective view of a stay partially assembled according to one embodiment of the present invention.

FIG. 8 illustrates another embodiment of the present invention wherein a pair of stays 58 is interconnected with a slotted connector 63 or hinge. A post 57 extends from a respective stay and is sized and configured so that the slotted connector 63 is positioned over each of the posts 57. In particular, the slotted connector 63 is generally a dog-boned shape having two slots 65 or openings defined to receive a respective post 57. The slots 65 defined in the slotted connector 57 are sized to allow each of the stays 58 to pivot and/or slide therein. Thus, each post 57 is capable of both pivoting and sliding within a respective slot 65 defined in the slotted connector 63. The slots 65 reduce binding between the posts 57 and slotted connector 63 during flexion and extension of the knee. The cooperation of the posts 57 and slotted connector 63 provides a "living hinge" that facilitates freedom of movement, i.e., flexion and extension of the knee. The two-point pivot of the stays 58 and slotted connector 63 closely mimics the natural flexion of the knee such that the stays provide stability without limiting the motion of the knee. In addition, the configuration of the stays 58 and slotted connector 63 reduces the incidence of binding between the slotted connector and the posts 57, which allows more freedom of movement of the knee during use. The slotted connector 63 is typically a polymeric material such as nylon but could be various materials capable of interconnecting the stays.

Additionally, FIGS. 5 and 8 show that the posts 57 extend from the inner surface of the stays 58 and are typically formed when securing the stays to the sheet of material 12. For instance, the stays 58 and posts 57 could be formed during the same injection-molding process. The slotted connector 63 is typically formed in a separate manufacturing process. The slotted connector 63 would then be positioned over the posts 57 and the posts pivotally attached thereto, such as by heat staking the posts to mushroom around the slots defined in the slotted connector. As such, the slotted connector 63 is pivotally attached to the stays 58.

It is understood that the slotted connector 63 and posts 57 shown in FIG. 8 are not meant to be limiting, as the slotted connector and posts could be various sizes and configurations while still providing stability and motion of the knee. Furthermore, the term "slotted connector" is not meant to be limiting, as hinges or similar mechanisms could be employed to interconnect a pair of stays 58 and provide pivotable and/or sliding motion therebetween. In addition, it is understood that the slotted connector 63, stays 58, and posts 57 could be formed with various processes, such as injection molding, and could be formed in the same operation if desired. For a further discussion of the interconnected stays, see U.S. patent application Ser. No. 11/609,105, entitled "Stay Hinge for Orthopedic Supports and Method of Using Same," which is assigned to the present assignee and incorporated herein by reference.

Figure 11:
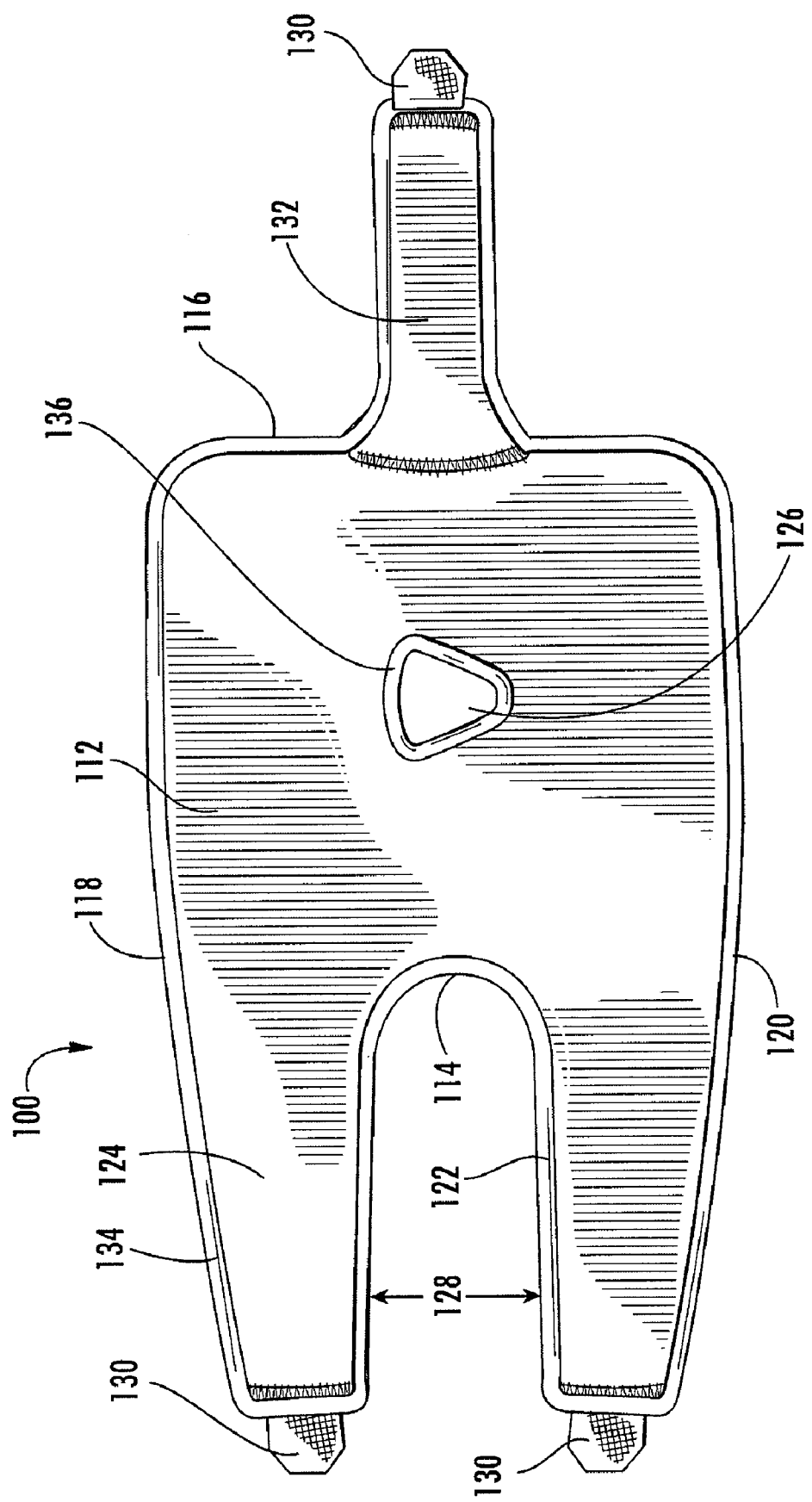
FIG. 11 is a plan view of a knee support according to another embodiment of the present invention, depicting edge material secured to a sheet of material.
Figure 12:
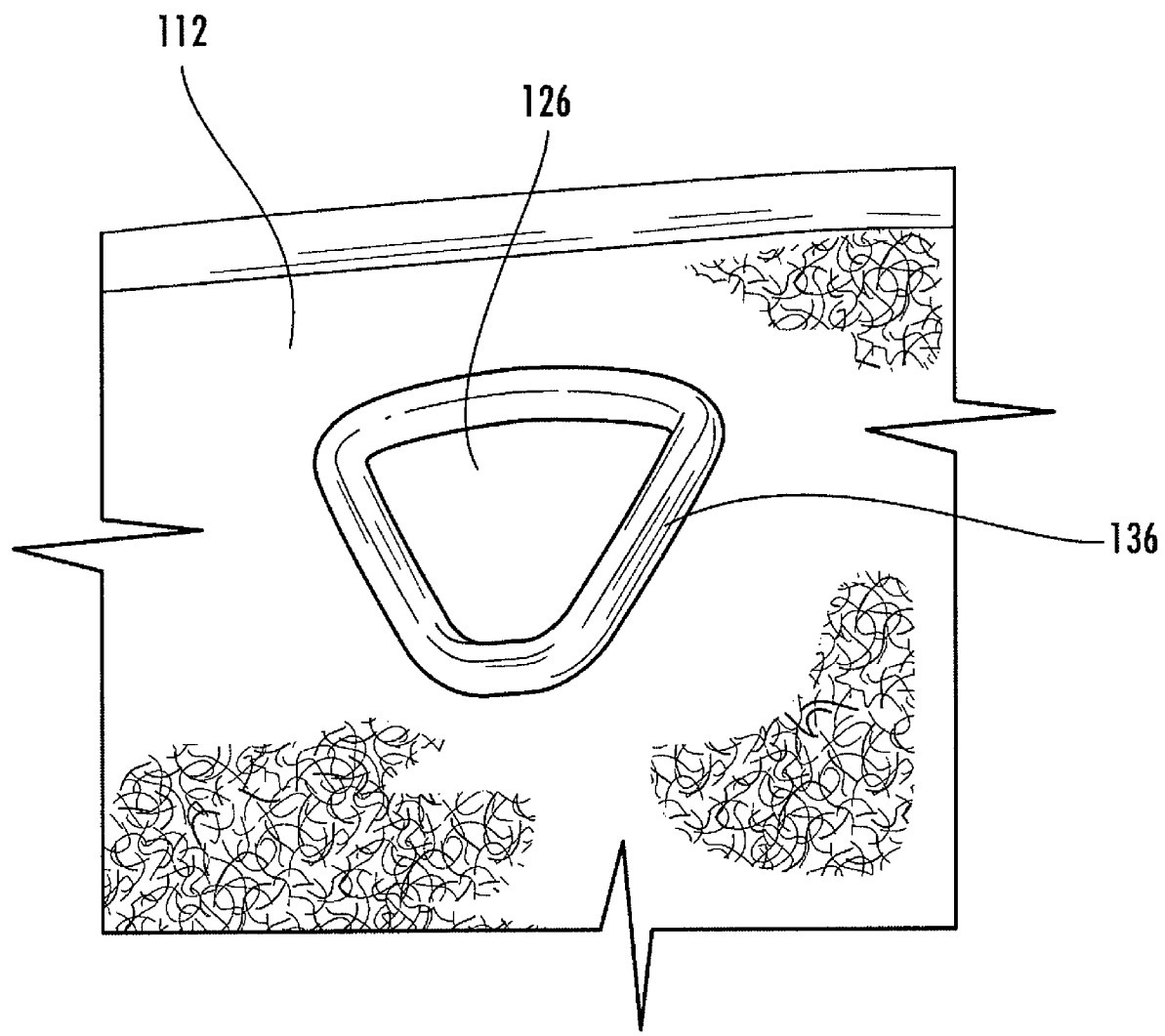
FIG. 12 is an enlarged view of a patellar opening of the knee support shown in FIG. 11 having edge material secured about its periphery.

FIGS. 11 and 12 illustrate another embodiment of the present invention. In particular, FIG. 11 illustrates a knee support 100 including an edge material 116 that is secured about the perimeter of the sheet of material 112, while FIG. 12 shows the edge material secured about the edge of the patellar opening 126. Thus, the edge material 116 encapsulates the edges of the sheet of material 112 in a similar fashion as that shown in FIG. 7. The edge material 116 is adaptable for use on various thicknesses of sheets of materials 112 that could be a laminate material (e.g., jersey, foam, and fleece laminate) or non-laminate material. The edge material 116 is pliable and resistant to fraying such that the edge material does not reduce the flexibility of the sheet of material 112 or irritate the skin. These characteristics make the edge material 116 useful for a range of orthopedic applications, such as braces, supports, bandages, straps, etc.

The edge material 116 is typically a soft and flexible polymeric material. For example, the edge material 116 could be thermoplastic elastomers such as Versaflex® (GLS Corporation), Dynaflex® (GLS Corporation), or Santoprene® (Advanced Elastomer Systems). Generally, the edge material 116 is injection molded or compression molded to the edges of the sheet of material 112. The edge material 116 is typically applied into a die in liquid form, compression molded or injection molded to the sheet of material 112, and trimmed to remove any excess edge material if required.

It is understood that the edge material 116 may be various sizes and configurations in aspects of the present invention. For instance, the edge material 116 may be secured at any number of locations on the sheet of material 112, such as proximate to areas that contact the wearer's skin and may be susceptible to irritation. The edge material 116 may be various thicknesses, and may be configured to provide different material properties, such as a high resistance to friction for preventing movement of the knee support 100 during use. Furthermore, there may be instances where decreased mobility is desired such that the edge material 116 is capable of providing rigidity for supporting the knee joint. For instance, the edge material 116 could be rigid for forming a splint-like support, where the edge material provides support for an injured area, and the sheet of material 112 remains soft and flexible for comfort.

The knee support 10 is applied to a wearer's knee area by positioning the support such that the patella registers with the patellar opening 26, and then wrapping the integral straps 22, 24 about the wearer's leg such that the upper strap 24 is positioned above the popliteal region of the knee and attaches to the sheet of material 12, and the lower strap 22 is positioned below the popliteal region and attaches to the sheet of material. The lateral edge strap 32 is then wrapped behind the knee until the fastening element 30 of the lateral edge strap overlaps lateral edge 14 and is secured to the complementary fastening material on the outer surface of the sheet of material 12. In this regard, the fastening elements 30 of the integral straps 22, 24 can be adjusted to the wearer's leg size by releasably securing the fastening elements to the outer surface of the sheet of material 12. When properly positioned, the inflatable bladder 34 provides cushioning and support about the wearer's patella. The flexible stays 58 provide bending resistance with flexion of the knee and medial/lateral support in order to support the knee area and prevent excessive movement thereof. Furthermore, the inflatable bladder 34 may be inflated or deflated to a desired pressure to provide cushioning and support on an opposite surface of the flexible stays.

Embodiments of the present invention may provide many advantages. For instance, the edge binding may be secured to the edges of the sheet of material for increasing comfort and/or support. Moreover, the edge binding eliminates additional material and fabrication steps to manufacture orthopedic supports, such as by eliminating stitching and pockets. The edge binding may be pliable and flexible or semi-rigid such that the edge binding is adaptable for various degrees of flexibility, support, and rehabilitation. Furthermore, the edge binding is adaptable for different orthopedic supports, such as a knee support.

The edge binding is capable of "grabbing" the edges of the sheet of material such that the edge binding may be secured to any number of locations on the sheet of material. In particular, the edge binding may be secured about the edges of the sheet of material to prevent fraying. The edge binding may be pliable such that the flexibility of sheet of material is not sacrificed. Moreover, the edge binding may also be configured as stays that may be formed at various locations on orthopedic supports for increasing support. The stays may be secured to the sheet of material within openings defined in the sheet of material by grabbing the edges of the openings. In addition, the positioning of the stays is capable of increasing the rehabilitative effects of various supports, such as by supporting the medial and lateral sides of the knee.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An orthopedic support comprising:
a sheet of flexible material configured to extend about and flexibly conform to at least a portion of a wearer's anatomy;
at least one strap attached to the sheet of material and configured to secure the sheet of flexible material about the portion of the wearer's anatomy; and
an edge binding comprising a polymeric material that is molded, but not stitched, to an edge of at least a portion of the sheet of flexible material, wherein the edge binding is configured to encapsulate the edge of the sheet of flexible material, and wherein the edge binding has a substantially C-shaped cross-section.

2. The orthopedic support according to claim 1, wherein the edge binding is molded about a periphery of an edge of an opening defined in the sheet of flexible material.

3. The orthopedic support according to claim 2, wherein the edge binding comprises at least one stay molded about the edge of a respective opening defined in the sheet of flexible material.

4. The orthopedic support according to claim 1, wherein the edge binding comprises a semi-rigid polymeric material.

5. The orthopedic support according to claim 1, wherein the edge binding comprises a flexible elastomeric material.

6. The orthopedic support according to claim 1, wherein the edge binding is molded along the edge about an outer periphery of the sheet of flexible material and is configured to flex with the sheet of flexible material and conform to the portion of the wearer's anatomy.

7. The orthopedic support according to claim 1, wherein the edge binding is compression molded or injection molded to the edge of the sheet of flexible material.

8. An orthopedic support comprising:
a sheet of flexible material configured to extend about and conform to at least a portion of a wearer's anatomy; and
at least one polymeric stay molded, but not stitched, about a periphery of an edge of a respective opening defined in the sheet of flexible material and configured to be positioned adjacent to a portion of the wearer's anatomy, wherein each stay has a substantially C-shaped cross-section about its periphery and is configured to encapsulate the edge of a respective opening.

9. The orthopedic support according to claim 8, wherein the sheet of flexible material is configured to at least partially enclose a leg of the wearer so that the sheet of flexible material extends around a knee of the wearer.

10. The orthopedic support according to claim 9, wherein a pair of integral straps extend from each of a distal and a proximal edge of the sheet of flexible material to define a gap therebetween, each integral strap configured to extend over a lateral edge of the sheet of flexible material and comprising a fastening element configured to attach to the sheet of material so as to secure the sheet of flexible material about the knee.

11. The orthopedic support according to claim 10, further comprising a medial strap attached to the sheet of flexible material and a fastening element, wherein the medial strap is configured to extend over a lateral edge opposite the pair of integral straps and through the gap, and wherein the fastening element is configured to attach to the sheet of flexible material so as to further secure the sheet of flexible material about the knee.

12. The orthopedic support according to claim 8, further comprising an air bladder secured to an inner surface of the sheet of flexible material and adjacent to at least a portion of the stay.

13. The orthopedic support according to claim 8, further comprising a plurality of stays each molded to an edge of a respective opening defined in the sheet of flexible material, the stays positioned on a medial and lateral side of a joint of the wearer.

14. The orthopedic support according to claim 13, wherein a pair of stays are aligned in a proximal-distal direction on each of the medial and lateral sides of the joint of the wearer.

15. The orthopedic support according to claim 8, wherein the stay is injection molded to the edge of a respective opening.

16. The orthopedic support according to claim 8, wherein each stay is generally trapezoidal in configuration.

17. The orthopedic support according to claim 8, wherein each stay comprises a straight lateral edge extending in a proximal-distal direction and an angled edge extending angularly from the proximal-distal direction.

18. The orthopedic support according to claim 8, wherein each stay comprises at least one reduced material portion that is of a thickness that is less than a thickness of a remaining portion of the stay.

19. The orthopedic support according to claim 8, further comprising an edge binding molded to an edge of at least a portion of the sheet of flexible material.

20. The orthopedic support according to claim 18, wherein the edge binding is molded along the edge about at least one of an opening in the sheet of flexible material and an outer periphery of the sheet of flexible material.

21. The orthopedic support according to claim 8, further comprising at least one strap attached to the sheet of flexible material and configured to extend over one of the lateral edges, wherein the strap comprises an associated fastening element configured to attach to the sheet of flexible material so as to secure the sheet about the portion of the wearer's anatomy.

22. A method comprising:
providing a sheet of flexible material configured to be positioned about and conform to a portion of a wearer's anatomy;
positioning the sheet of flexible material within a mold; and
supplying a liquid polymeric material within the mold so as to mold an edge binding along an edge of at least a portion of the sheet of flexible material and so as to encapsulate the edge with the edge binding.

23. The method according to claim 22, wherein supplying comprises injection molding or compression molding the edge binding along the edge.

24. The method according to claim 22, wherein supplying comprises molding the edge binding about a periphery of an edge of an opening defined in the sheet of material.

25. The method according to claim 24, wherein supplying comprises molding at least one stay about the periphery of the edge of a respective opening defined in the sheet of flexible material.

26. The method according to claim 22, wherein supplying comprises molding along the edge about an outer periphery of the sheet of flexible material.

\* \* \* \* \*